United States Patent
Quintana Muñoz

(10) Patent No.: US 6,592,828 B2
(45) Date of Patent: Jul. 15, 2003

(54) RECHARGEABLE ELECTRIC AIR-FRESHENER FOR CARS

(76) Inventor: José Quintana Muñoz, Murillo, 43, 3°3ª, Cornella de Llobregat (Barcelona) (ES)

( * ) Notice: Subject to any disclaimer, the term of this patent is extended or adjusted under 35 U.S.C. 154(b) by 0 days.

(21) Appl. No.: 10/154,501

(22) Filed: May 24, 2002

(65) Prior Publication Data

US 2002/0176810 A1 Nov. 28, 2002

(30) Foreign Application Priority Data

May 28, 2001 (ES) ..................................... 200101393 U

(51) Int. Cl.$^7$ ................................................. A61L 7/03
(52) U.S. Cl. .......................... 422/125; 422/5; 422/123; 392/390; 392/391
(58) Field of Search ................................. 422/125, 123, 422/305, 307, 5; 392/390, 392, 394, 391, 395

(56) References Cited

U.S. PATENT DOCUMENTS

| | | | | |
|---|---|---|---|---|
| 5,373,581 A | * | 12/1994 | Smith | 392/390 |
| 5,394,506 A | * | 2/1995 | Stein et al. | 392/395 |
| 5,626,496 A | * | 5/1997 | Hahn | 439/668 |
| 5,788,931 A | * | 8/1998 | Munoz Quintana | 422/125 |
| 6,141,496 A | * | 10/2000 | Sundberg et al. | 392/390 |
| 6,197,263 B1 | * | 3/2001 | Blount | 422/125 |
| 6,249,645 B1 | * | 6/2001 | Smith | 392/403 |

\* cited by examiner

Primary Examiner—Robert J. Warden, Sr.
Assistant Examiner—Sean Conley
(74) Attorney, Agent, or Firm—Richard M. Goldberg

(57) ABSTRACT

Rechargeable electric air-freshener for vehicles, of a type which is placed in a lighter holder of these vehicles includes a case, a lid for closing the case, each provided with openings for the perfuming vapor from an aromatic substance, which may be recharged and which, by means of temperature, releases aromatic essences it contains, situated inside the case, two metal bands on sides of the case to hold the case in position, one permitting connection to one electrical pole, a button at a rear portion of the case, a spring inside the case for the other pole, an integrated printed heated electrical circuit in the case, and an external button with four positions for activating the electrical circuit, the external button including an LED visible behind the lid and a switch, which activates a sound alarm to advise of a need to recharge the aromatic substance.

1 Claim, 1 Drawing Sheet

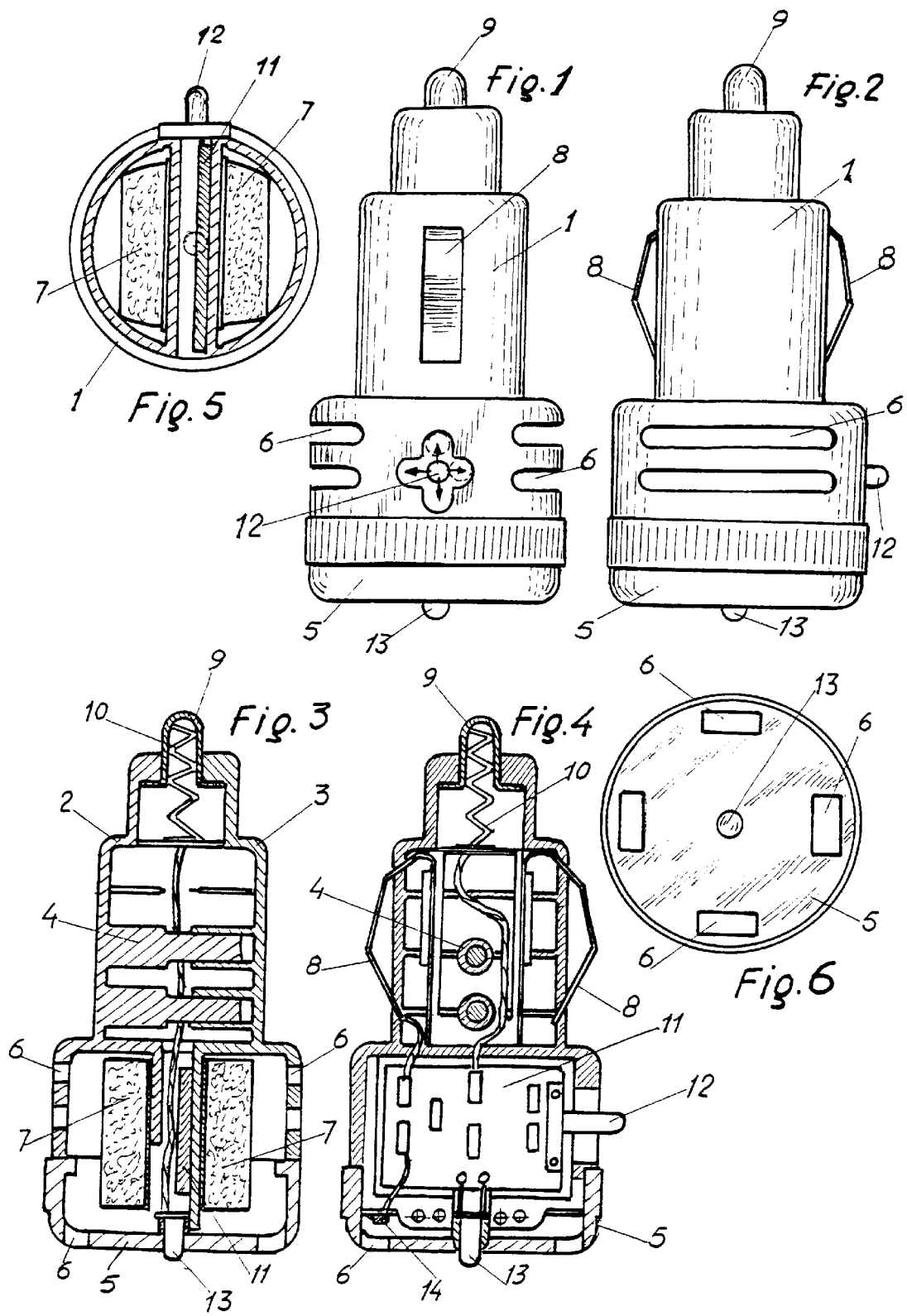

RECHARGEABLE ELECTRIC AIR-FRESHENER FOR CARS

BACKGROUND OF THE INVENTION

The present patent refers to a rechargeable electric air-freshener for cars, of the type which are activated electrically by being positioned inside the lighter located in the control deck or, in some vehicles, in an additional connection with similar features. The advantage of this rechargeable electric lighter, which distinguishes it from those which are currently in use, is the fact that it may be switched on and switched off, thus stopping the emission of the odour, with the aid of a simple electrical device endowed with an incorporated external activation button.

The use of devices which emit pleasant odours inside the car with the intention of masking the bad smells that may arise in a closed compartment is nothing new, for relatively uncomplicated devices supplied with solids which sublimate on contact with the atmosphere have been used for many years, both in cars and in houses and places of work.

A further advance in this sector was made with the appearance of devices supplied with liquid or solid odorants, the evaporation of which was produced by being electrically heated once positioned in the place of the car lighter in such a way that, when the user inserted it into the correct position, the resistor contained within the device was activated when its poles came into contact with the electrical terminals located inside the lighter case for the purposes of the latter's activation.

SUMMARY OF THE INVENTION

The rechargeable electric air-freshener for cars, which constitutes the basis of the herein invention, belongs to this latter type. The main features which distinguish it from those currently in use are the greater robustness of its construction, which makes it more reliable, and the fact that it contains a small integrated printed and heated circuit, activated by an external button with four positions, which enables it to be switched on and off and, in the intermediate positions, to produce a greater or lesser intensity of perfume. This is not possible with the existing devices, which have to be removed from the lighter holder and have a place found for their storage, if it is not desired that they emit an aroma. Apart from being bothersome and complicated, given the small amount of room available inside the car for storing things, it is then difficult to find again, for it cannot always be put away in the same place.

Thus it is that the claimed device is set inside a case with a lid endowed with openings for the aroma to come out of. Its measurements permit it to be lodged in the car lighter holder or additional connection, and it is equipped with a contact button in its rear and two metal bands on its sides to hold it in place, one of which establishes the electrical contact, all which enables a perfect connection with the lighter's electrical terminals and permits the activation of the integrated printed and heated electrical circuit which it contains. The latter comes complete with an LED and a switch visible behind the lid for activating a sound alarm indicating how long the odorant will last. The fixed LED indicates functions by means of coloured and intermittent light, to give visual warning of the need to recharge the odorant substance.

In order to make this explanation clearer, a sheet of non-restrictive drawings is attached to the herein specification showing, for the purposes of illustration, an example of the embodiment of a rechargeable electric air-freshener for cars, in accordance with the principles of the claim.

BRIEF DESCRIPTION OF THE DRAWINGS

In the drawings:

FIGS. 1 and 2 show a front and side view respectively of outside of the rechargeable electric air-freshener for cars as claimed, while FIGS. 3 and 4 show internal cross-sections of the same views.

As for FIG. 5, it shows a horizontal cross-section of the cylindrical part of the air-freshener which holds the perfuming substance.

Finally, in FIG. 6 may be seen a horizontal cross-section of the lower part of the device.

DETAILED DESCRIPTION

As may be deduced from the cited sheet of drawings, the rechargeable electric air-freshener for cars as claimed is composed of an outer case -1- formed by two halves -2- and -3-, joined laterally by projecting elements -4-, which fix and close them at the rear by means of a screw-lid -5-, which enables it to be fixed to control deck. It is planned for all these pieces to have openings -6- to permit the emergence of the aroma which issues from a solid, liquid, or gel-type substance, which has the advantage of being rechargeable -7-, housed within.

Along each aide of the case emerge metal bands -8- to fix it correctly, one of which establishes an electrical contact, while the other pole is achieved with a button -9-, which sticks out to the rear of the device. In addition, a spring -10- is inside the case for the other electrical pole, the spring being in contact with the button -9-.

In order to achieve the evaporation of the perfuming substance, a printed and heated integrated electrical circuit -11- has been devised which is activated externally by means of a button with four connections -12-, one for opening and closing and one each, when opened, for greater or lesser emission of scent. It is also planned for an LED -13- and a switch visible behind the lid -14- to be joined to this circuit. This LED -13- is fixed and indicates functions with the aid of a coloured and intermittent light, when set for a visual alarm, in order to advise of the need to recharge. The switch -14- activates a sound alarm indicating the duration of the recharged aromatic substance.

The foregoing specification permits the claimed device's operating system and its differences with respect to those currently in existence to be easily understood.

Thus, when the rechargeable electric air-freshener is placed in the car lighter's holder, it remains more securely connected than those currently in existence, since all the connections are provided with metal bands which serve as pressure springs, thus ensuring that, although the car passes over irregular road surfaces, the terminals are always in contact and the device ready to work at any moment.

What is more, the air-freshener may be maintained in its position of connection for a long time, whether we want it to operate or not, since the activating button in collaboration with the electrical circuit it contains allows it to be in or out of service, and even for different strengths of odour to be activated. None of this is possible in the devices that currently exist since, when put into contact with the car's electrical circuit, they are set into operation with a single flow of vapour emission and, in order for them to stop working, it is necessary to disconnect them.

Finally, the existence of an LED which indicates when it is in operation with different colours according to the different positions of activation and which becomes intermittent when the aromatic substance needs recharging, as well as activating a sound alarm if the corresponding switch is activated, constitutes a further advantage which, together with those described above, mean that the claimed rechargeable electric air-freshener for car represents a significant innovation in its field.

What is claimed is:

1. Rechargeable electric air-freshener for vehicles, of a type which is placed in a lighter holder of these vehicles or in an additional existing connection and connected to an electrical circuit of the vehicles, comprised of:

- a case,
- a lid for closing the case,
- the case and the lid each provided with openings to permit the emergence of perfuming vapor which proceeds from a solid, liquid or gel-type substance, which may be recharged and which, by means of temperature, releases aromatic essences it contains, situated inside the case,
- two metal bands on sides of the case to hold the case in position, one of which permits connection to one electrical pole,
- a button at a rear portion of the case,
- a spring inside the case for the other pole, the spring being in contact with the button,
- an integrated printed heat electrical circuit in the case,
- an external button with four positions for activating the electrical circuit, the four positions including an on position, an off position, and two intermediate positions to produce different intensities of release of the aromatic essences position corresponding to movement of the external button different direction,
- a light emitting diode visible behind the lid, and
- a switch which, when activated, activates a Sound alarm to advise of a need to recharge the aromatic substance,
- the external button, light emitting diode and switch being the external connected to the integrated printed heated electrical circuit.

* * * * *